United States Patent [19]

Spooner

[11] Patent Number: 5,922,279
[45] Date of Patent: Jul. 13, 1999

[54] TREATMENT OF CONTACT LENSES WITH AN AQUEOUS SOLUTION INCLUDING PYRROLIDONE COMPOUNDS

[75] Inventor: Susan P. Spooner, Rochester, N.Y.

[73] Assignee: Bausch & Lomb Incorporated, Rochester, N.Y.

[21] Appl. No.: 08/796,400

[22] Filed: Feb. 6, 1997

Related U.S. Application Data

[60] Provisional application No. 60/012,385, Feb. 28, 1996.
[51] Int. Cl.[6] .............................. A61L 2/18; C07D 295/00
[52] U.S. Cl. ............................. 422/28; 548/400; 548/579; 514/840
[58] Field of Search ................................ 422/28; 548/400, 548/579; 514/840

[56] References Cited

U.S. PATENT DOCUMENTS

| | | |
|---|---|---|
| 4,687,816 | 8/1987 | Lin et al. . |
| 4,758,595 | 7/1988 | Ogunbiyi et al. ........................ 514/635 |
| 5,035,859 | 7/1991 | Gu et al. ..................................... 422/28 |
| 5,096,607 | 3/1992 | Mowrey-McKee ...................... 252/106 |
| 5,640,980 | 6/1997 | Keene et al. ............................ 134/58 R |

FOREIGN PATENT DOCUMENTS

| | | |
|---|---|---|
| 646641 | 4/1995 | European Pat. Off. . |
| 5-186798 | 7/1993 | Japan . |
| 8-133911 | 5/1996 | Japan . |

OTHER PUBLICATIONS

Ash et al, Handbook of Cosmetic and Personal Care Additives, p. 435, 1994.

*Primary Examiner*—Elizabeth McKane
*Attorney, Agent, or Firm*—Chris P. Konkol

[57] ABSTRACT

The present invention provides methods for treating contact lenses and compositions for the same. The present invention includes contacting a lens with an aqueous solution comprising a pyrrolidone compound represented by the formula:

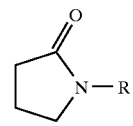

wherein: R is a hydrogen or an alkyl group having from 1 to 6 carbon atoms. In preferred embodiments of the invention, the subject compounds are used in combination with antimicrobial agents for providing simultaneous disinfection and cleaning of contact lenses.

12 Claims, No Drawings

TREATMENT OF CONTACT LENSES WITH AN AQUEOUS SOLUTION INCLUDING PYRROLIDONE COMPOUNDS

This application claims the benefit of U.S. Provisional Application No. 60/012,385 filed on Feb. 28, 1996.

FIELD OF THE INVENTION

The present invention is directed toward methods for treating contact lenses and compositions for the same. The subject invention includes the use of an aqueous solution including certain pyrrolidone compounds, described below. Preferred embodiments of the invention include methods and compositions for simultaneously cleaning and disinfecting contact lenses.

BACKGROUND

In the normal course of wearing contact lenses, tear film and debris consisting of proteinaceous, oily, sebaceous, and related organic matter have a tendency to deposit and build up on lens surfaces. As part of the routine care regimen, contact lenses must be cleaned to remove these tear film deposits and debris. If these deposits are not properly removed, both the wettability and optical clarity of the lenses are substantially reduced causing discomfort for the wearer.

Further, contact lenses, especially those made from hydrophilic materials, must be continuously disinfected to kill harmful microorganisms that may be present or grow on the lenses. A number of methods for disinfecting contact lenses have been used such as the use of high temperatures, the use of oxidative chemicals, and the use of antimicrobial agents.

Conventionally, the cleaning of contact lenses is accomplished with one or both of two general classes of cleaners. Surfactant cleaners, generally known as "daily cleaners" because of their recommended daily use, are effective for the removal of most carbohydrate and lipid derived matter. However, they are not as effective for the removal of proteinaceous matter such as lysozyme. Typically, proteolytic enzymes derived from plant, animal, and microbial sources are used to remove the proteinaceous deposits. These "enzyme" cleaners are typically recommended for weekly use and are conventionally employed by dissolving enzyme tablets in suitable aqueous solutions.

The process of cleaning and disinfecting contact lenses typically involves several steps. The first steps typically comprise the cleaning phase whereby lenses are conventionally soaked in an enzyme cleaning solution at ambient temperature conditions, i.e., soaking for a period of up to 12 hours, to achieve effective removal of proteinaceous deposits, followed by rubbing the lens with a daily cleaner to further remove debris. After cleaning, the lenses are typically disinfected. Disinfection involves contacting the lenses with a solution containing an oxidative chemical (e.g. hydrogen peroxide) or an antimicrobial agent at ambient temperatures. Alternatively, disinfection may be accomplished by exposing the lenses to elevated temperatures for specified periods of time. This latter disinfection technique requires the use of a common electrical disinfecting apparatus.

Methods have been developed which can remove proteinaceous material from contact lenses while simultaneously disinfecting the lenses. For example, U.S. Pat. No. 4,614,549 discloses a single-step method of cleaning and disinfecting contact lenses in aqueous solutions of proteolytic enzymes at temperatures of between 60° C. and 100° C. Unfortunately, this method requires the use of an electrical disinfecting apparatus and elevated temperatures. Another example of a method for simultaneously cleaning and disinfecting contact lenses is described in U.S. Pat. No. Re. 32,672 which discloses a method wherein lenses are immersed in a solution containing peroxide and a peroxide active enzyme. However, this method requires an additional step of neutralization of the residual peroxide prior to inserting the lens into the eye.

In an effort to provide greater convenience, new regimens have been developed. For example, Bausch & Lomb offers a cleaning and disinfection system wherein lenses are simultaneous cleaned and disinfected by immersing the lens within ReNu® Multi-purpose Solution including a ReNu® enzymatic tablet (see for example U.S. Pat. No. 5,096,607 issued Mar. 17, 1992). This system provides the benefit of combined "daily" cleaning and disinfection in one solution, wherein the same solution may be directly used in combination with enzymatic cleaners, thus reducing the number of steps and components required for effective lens cleaning and disinfection.

Although the above-described Bausch & Lomb cleaning regimen offers significant convenience over prior art systems, further convenience is sought. More specifically, it is desired to provide a single solution capable of providing cleaning comparable with systems which utilize enzymatic cleaners.

SUMMARY OF THE INVENTION

The present invention includes methods for treating contact lenses and compositions for the same. The present invention includes contacting a lens with an aqueous solution comprising a pyrrolidone compound represented by the formula:

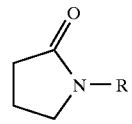

wherein: R is a hydrogen or an alkyl group having from 1 to 6 carbon atoms.

The subject compounds may be used in combination with antimicrobial agents for providing simultaneous disinfection and cleaning of contact lenses. In preferred embodiments of the present invention, the subject composition provides a one step cleaning regimen which utilizes only one solution, and which provides comparable protein removal as cleaning regimens using enzymatic cleaning. Furthermore, in preferred embodiments, the subject composition also provides a solution which can be used directly in the eye. As such, the present invention offers significant advantages over known cleaning and disinfecting regimens.

DETAILED DESCRIPTION OF THE INVENTION

The present invention can be used with all contact lenses such as conventional hard, soft (hydrophilic), rigid and soft gas permeable, and silicone (including both hydrogel and non-hydrogel) lenses, but is preferably employed with soft (hydrophilic) lenses. Such lenses are commonly prepared from monomers such as hydroxyethylmethacrylate, hydroxyethylmethyl methacrylate, vinylpyrrolidone, glycerolmethacrylate, methacrylic acid or acid esters and the like. Such lenses absorb significant amounts of water such as from about 4 to about 80 percent by weight.

As previously indicated, the present invention includes an aqueous solution comprising a pyrrolidone compound represented by the Formula I:

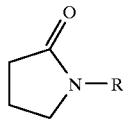
(I)

wherein R is a hydrogen or an alkyl group having from 1 to 6 carbon atoms which may be unsubstituted or substituted (e.g. with hydroxyl groups, alkyl groups, etc.). More preferably R is an an alkyl group having 1 to 4 carbon atoms, most preferably 1 or 2 carbon atoms. An example of a preferred compound is 1-methyl-2-pyrrolidinone, available from International Specialty Products in Wayne, N.J. under the mark Pharmasolve™.

This compound may be represented by Formula II:

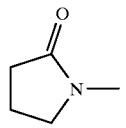
(II)

This compound is known for use in improving the solubility of drugs in pharmaceutical formulations and drug delivery systems.

The use of $C_8$ through $C_{20}$ N-alkyl-2-pyrrolidone compounds as microbicidial agents in contact lens solutions is disclosed U.S. Pat. No. 5,035,859 to Gu et al. Because of their long aliphatic chains, i.e. $C_8$ through $C_{20}$, these materials function as surfactants. Unlike these long chain pyrrolidones, the subject pyrrolidone compounds are thoroughly dispersed in aqueous solutions and are believed to solublize and remove protein material from the lens. This property is not present with the long chain pyrrolidone compounds.

Although lesser quantities can be used (e.g. 0.001 percent weight by volume), the subject aqueous solution preferably includes at least about 0.01 percent weight by volume the subject pyrrolidone compound.

The subject aqueous solution may also contain various other components including, but not limited to: antimicrobial agents, buffering agents, chelating and/or sequestering agents, tonicity adjusting agents, and surfactants. Furthermore, the subject solution preferably has a pH of between about 6 to about 8, and more preferably between 7 to 7.5.

For the purpose of this patent, the term tonicity adjusting agents refer to those agents which are used to modify the osmololality of a formulation. Examples of suitable tonicity adjusting agents include, but are not limited to: sodium and potassium chloride, dextrose, and calcium and magnesium chloride. These agents are typically used individually in amounts ranging from about 0.01 to 2.5% (w/v) and preferably, form about 0.5 to about 1.5% (w/v). Preferably, the tonicity agent will be employed in an amount to provide a final osmotic value of less than about 350 mOsm/kg and more preferably between about 250 to about 350 mOsm/kg, and most preferably between about 280 to about 320 mOsm/kg.

Suitable surfactants can be either cationic, anionic, nonionic or amphoteric. Preferred surfactants are neutral or nonionic surfactants which may be present in amounts up to about 5% (w/v). Examples of suitable surfactants include, but are not limited to: polyethylene glycol esters of fatty acids, polyoxypropylene ethers of $C_{12}$–$C_{18}$ alkanes and polyoxyethylene-polyoxypropylene block copolymers of ethylene diamine (i.e. poloxamine).

Examples of preferred chelating agents include ethylenediaminetetraacetic acid (EDTA), and its salts (sodium) which are normally employed in amounts from about 0.024 to about 2.0% (w/v). Other known chelating (or sequestering agents) such as certain polyvinyl alcohols can also be used.

The subject solution preferably includes at least one antimicrobial agent. As used herein, the term antimicrobial agent is intended to mean non-oxidative organic chemicals which derive their antimicrobial activity through a chemical or physicochemical interaction with organisms. Suitable antimicrobial agents including quaternary ammonium salts. Examples of suitable quaternary ammonium salts for use in the present invention include, but are not limited to: poly [(dimethyliminio)-2-butene-1,4-diyl chloride], [4-tris(2-hydroxyethyl) ammonio]-2-butenyl-w-[tris(2-hydroxyethyl) ammonio] dichloride (chemical registry no. 75345-27-6) generally available as Polyquaternium 1® from ONYX Corporation. Other applicable antimicrobial agents include biguanides such as salts of alexidine. Particularly preferred antimicrobial agents include hexamethylene biguanides, including their water soluble polymers, e.g. polyaminopropyl biguanide, having a molecular weight of up to about 100,000. Such compounds are quite well known and are described in various references including, for example, U.S. Pat. No. 4,758,595. One particularly preferred material is PHMB, available form ICI Americas, Inc., Wilmington Del. under the mark Cosmocil CQ.

If used in the subject solution, the antimicrobial agent should be used in an amount which will at least partially reduce the microorganism population in the formulations employed. Preferably, a disinfecting amount is that which will reduce the microbial burden by two log orders in four hours and more preferably by one log order in one hour. Most preferably, a disinfecting amount is an amount which will eliminate the microbial burden on a contact lens when used in regimen for the recommended soaking time (FDA Chemical Disinfection Efficacy Test-July, 1985 Contact Lens Solution Draft Guidelines). Typically, such agents are present in concentrations ranging from about 0.00001 to about 0.5% (w/v), and more preferably, from about 0.00003 to about 0.05% (w/v).

As stated, contact lenses are cleaned by contacting the lens with the subject aqueous solution. Although this may be accomplished by simply soaking a lens in the subject solution, greater cleaning can be achieved if a few drops of the solution are initially placed on each side of the lens, and the lens is rubbed for approximately 20 seconds. The lens is then subsequently immersed within several milliliters of the subject solution. Preferably, the lens is permitted to soak in the solution for at least four hours. Furthermore, the lenses are preferably rinsed with fresh solution after the rubbing step and after being immersed within the solution. If the subject solution includes antimicrobial agent, the subject solution not only cleans the lens, but also disinfects. However, it will be appreciated that the subject aqueous solution need not include an antimicrobial agent, and other disinfection means may be used in combination therewith, e.g. heat disinfection, oxidation disinfection e.g. hydrogen peroxide, etc.

Although not necessary, enzymatic cleaners may also be used with the subject solution treating contact lenses. If used, enzymatic tablets may be placed directly within the subject solution, is a manner like that described in U.S. Pat. No. 5,096,607.

As an illustration of the present invention, several examples are provided below. These examples serve only to further illustrate aspects of the invention and should not be construed as limiting the invention.

EXAMPLES

An example of a preferred formulation of the subject invention is provided below in Table I. This solution was prepared by weighing out the necessary amount of concentrated Pharmasolve™ into a glass beaker, followed by bringing the solution up to total volume with ReNu® Multi-Purpose Solution. The pH of the resulting solution was between about 7.1 to 7.3. (If necessary, the pH of the solution may be adjusted by use of an appropriate amount of hydrochloric acid or sodium hydroxide, as indicated in Table I).

TABLE I

| Constituent | % Weight by Volume |
|---|---|
| Polyhexamethylene biguanide HCl (as a 20% w/w solution available under the mark Cosmocil CQ, from ICI Chemical Co.) | .00047 |
| Boric Acid | 0.64 |
| Sodium Borate | 0.12 |
| Edetate Disodium | 0.11 |
| Sodium Chloride | 0.49 |
| Poloxamine (Tetronic ® 1107 from BASF Co.) | 1.00 |
| Pharmasolve ™ | 0.10 |
| Hydrochloric Acid, 1N | as required for pH adjustment |
| Sodium Hydroxide, 1N | as required for pH adjustment |
| Purified Water | Balance to 100 |

In order to further illustrate the subject invention, a number of soft hydrogel (FDA group III, bulifcon A) lenses were coated with protein deposits followed by treatment with one of several test solutions (as described in Table I, including various amounts of Pharmasolve). These lenses were then compared with lenses treated with a Control solution consisting of ReNu® MPS with ReNu® 1 step enzymatic tablets.

PROTEIN DEPOSITION

Lenses were coated with an in-vitro protein deposit procedure which consisted of first preparing an aqueous electrolyte solution consisting of approximately 0.70% sodium chloride, 0.17% potassium chloride, 0.22% sodium bicarbonate, and 0.0005% of calcium chloride, dihydrate. The solution was prepared by adding the chlorides and bicarbonate to approximately 90% of the total volume of distilled water required, followed by thorough mixing of the solution. The pH was measured and, if necessary, adjusted to 7.2+/−0.1 with either 1N HCl or 1N NaOH. The solution had an osmolality of between 280 to 320 mOsm/kg. An appropriate amount of lysozyme was then added to the electrolyte solution so that the solution had a 0.10% concentration of lysozyme. The resulting solution was mixed for approximately thirty minutes at moderate speed. The pH was measured (and if necessary, adjusted to 7.2+/−0.1 with either 1N HCl or 1N NaOH).

A borate buffered saline solution was also prepared, comprising approximately 0.85% boric acid, 0.09% sodium borate, and 0.45% of sodium chloride. The pH was measured (and if necessary, adjusted to 7.2+/−0.1 with either 1N HCl or 1N NaOH). The osmolality of the solution was between 280 to 320 mOsm/kg.

Protein deposits were coated upon a number soft hydrogel lenses by placing each lens within a glass vial followed by submerging the lenses in approximately 5 ml of the protein solution. The vials were then capped and subjected to shaking in a thermal water bath at approximately 80° C. for about twenty minutes. Subsequently, the lenses were allowed to cool to ambient temperature, followed by gently rubbing the lenses with the borate buffered saline to remove any loosely bound protein.

LENS TREATMENT

Once coated with protein, the lenses were subjected to treatment with either one of the subject solutions or the Control solution. Treatment with the subject solutions consisted of placing several drops of the test solution on both sides of the lens followed by rubbing the lens for approximately twenty seconds. The lenses were then rinsed with the test solution and soaked in approximately 5 ml of test solution for four hours. The lenses were then rinsed with a borate buffered saline.

Treatment with the Control solution consisted of placing several drops of ReNu® MPS on both sides of the lens followed by rubbing the lens for approximately twenty seconds. The lenses were then rinsed with fresh ReNu® MPS and soaked in approximately 10 ml of ReNu® MPS including one ReNu® enzyme tablet for approximately four hours. The lenses were subsequently rubbed and rinsed with fresh ReNu® MPS and finally rinsed with borate buffered saline.

MICROSCOPIC IMAGE ANALYSIS

Following treatment, the lenses were evaluated using microscopic image analysis to determine the amount of protein removed as a result of treatment. The results of this evaluation are provided in Table II, below.

The microscopic image analysis consisted of digitally photographing the lenses and analyzing surface debris by gray scale image analysis. This procedure involved placing each lens under a microscope having a "dark field" background and subsequently passing incident light through the lens. Surface debris on the lens scatters light and appears lighter than the clean surface on the contact lens. A digital image of the illuminated lens is obtained and the pixels are counted/separated based on their intensities. The intensity value of each lens treated with a test solution was then compared with that of lenses treated with the Control solution. From this data, the relative protein removal for each lens was determined is indicated in Table II as a percent change in density compared with the Control solution.

TABLE II

| Example No. | % Change in Pixel Density Relative to Control (Control = 100%) |
|---|---|
| 1 (0.01% Pharmasolve ™) | 60% |
| 2 (0.01% Pharmasolve ™) | 86% |
| 3 (0.01% Pharmasolve ™) | 66% |
| 4 (0.05% Pharmasolve ™) | 111% |
| 5 (0.05% Pharmasolve ™) | 61% |
| 6 (0.10% Pharmasolve ™) | 90% |
| 7 (0.10% Pharmasolve ™) | 121% |

TABLE II-continued

| Example No. | % Change in Pixel Density Relative to Control (Control = 100%) |
|---|---|
| 8 (0.10% Pharmasolve ™) | 68% |
| 9 (0.50% Pharmasolve ™) | 105% |
| 10 (0.50% Pharmasolve ™) | 70% |

*Each example is based upon data collected from ten lenses treated in identical manner.

As is shown by the data provided in table II, the subject solutions and methods for treating lenses provided comparable protein removal to that of the control solution (which including the use of enzymatic cleaning).

In addition to providing excellent cleaning, the subject solution also provided comparable disinfection as the Control solution.

I claim:

1. A method for treating contact lenses comprising contacting a lens with a composition comprising, in the absence of a proteolytic enzyme, the following separate ingredients:
   (a) an effective amount of a pyrrolidone compound represented by the formula:

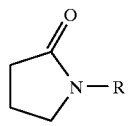

wherein R is a hydrogen or an alkyl group having from 1 to 6 carbon atoms;
   (b) 0.00003 to 0.05% weight per volume of an antimicrobial agent; and
   (c) an effective amount of a cationic, anionic, nonionic, or amphoteric surfactant; wherein the composition is an aqueous solution having a pH from about 6 to about 8 and an osmolality of between about 250 to 350 mOsm/kg.

2. The method of claim 1 wherein R is an alkyl group having from 1 to 4 carbon atoms.

3. The method of claim 1 wherein R is an alkyl group having 1 carbon atom.

4. The method of claim 1 wherein the antimicrobial agent is a polyaminopropyl biguanide.

5. The method of claim 1 wherein said contacting of a lens with said solution comprises rubbing the lens with the solution, followed by immersing the lens within the solution.

6. A composition for treating contact lenses comprising, in the absence of a proteolytic enzyme, the following separate ingredients:
   (a) an effective amount of a pyrrolidone compound represented by the formula:

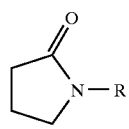

wherein R is a hydrogen or an alkyl group having from 1 to 6 carbon atoms;
   (b) 0.00003 to 0.05% weight per volume of an antimicrobial agent; and
   (c) an effective amount of a cationic, anionic, nonionic, or amphoteric surfactant;

wherein the composition is an aqueous solution having a pH from about 6 to about 8 and an osmolality of between about 250 to 350 mOsm/kg.

7. The solution of claim 6 wherein R is an alkyl group having from 1 to 4 carbon atoms.

8. The solution of claim 6 wherein R is an alkyl group having 1 carbon atom.

9. The solution of claim 6 wherein the concentration of the pyrrolidone compound is at least 0.01 percent weight by volume.

10. The solution of claim 5 wherein said antimicrobial agent is a polyaminopropyl biguanide.

11. The solution of claim 10 further comprising PHMB.

12. A method for treating contact lenses comprising contacting a lens with a composition comprising, in the absence of a proteolytic enzyme, the following separate ingredients:
   (a) an effective amount of a pyrrolidone compound represented by the formula:

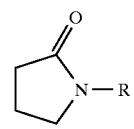

wherein R is an alkyl group having from 1 to 6 carbon atoms;
   (d) 0.00003 to 0.05% weight per volume of an antimicrobial agent; and
   (e) an effective amount of a cationic, anionic, nonionic, or amphoteric surfactant;

wherein the composition is an aqueous solution having a pH from about 6 to about 8 and an osmolality of between about 250 to 350 mOsm/kg.

* * * * *

UNITED STATES PATENT AND TRADEMARK OFFICE
CERTIFICATE OF CORRECTION

PATENT NO. : 5,922,279
DATED : Jul. 13, 1999
INVENTOR(S) : Susan P. Spooner

It is certified that error appears in the above-identified patent and that said Letters Patent is hereby corrected as shown below:

In Column 8, line 26, "claim 5" should read -- claim 6 -- .

Signed and Sealed this

Eleventh Day of July, 2000

Attest:

Q. TODD DICKINSON

*Attesting Officer*  *Director of Patents and Trademarks*